(12) United States Patent
Fontius

(10) Patent No.: US 9,468,395 B2
(45) Date of Patent: Oct. 18, 2016

(54) MEDICAL UNIT AND METHOD FOR IMPROVING EXAMINATION AND TREATMENT WORKFLOWS

(75) Inventor: Jörg Ulrich Fontius, Neunkirchen A. Brand (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 2290 days.

(21) Appl. No.: 12/321,907

(22) Filed: Jan. 27, 2009

(65) Prior Publication Data
US 2009/0192384 A1 Jul. 30, 2009

(30) Foreign Application Priority Data
Jan. 30, 2008 (DE) .................. 10 2008 006 711

(51) Int. Cl.
*A61B 5/05* (2006.01)
*A61B 5/055* (2006.01)
(Continued)

(52) U.S. Cl.
CPC ............. *A61B 5/0555* (2013.01); *A61B 5/721* (2013.01); *A61B 6/527* (2013.01); *A61B 6/5264* (2013.01); *G01S 13/88* (2013.01); *A61B 5/7285* (2013.01); *A61B 6/03* (2013.01); *A61B 6/541* (2013.01); *A61B 34/20* (2016.02);
(Continued)

(58) Field of Classification Search
CPC .................... A61B 5/7239; A61B 2562/0219; A61B 8/00; A61B 6/541; A61B 5/7292; A61B 5/113; A61B 5/055; A61B 8/543; A61B 5/7285; A61B 5/1102
USPC .................. 600/413, 421; 128/898
See application file for complete search history.

(56) References Cited

U.S. PATENT DOCUMENTS 5,852,672 A * 12/1998 Lu .................................. 382/154
7,196,629 B2 3/2007 Ruoss et al.
(Continued)

FOREIGN PATENT DOCUMENTS

DE 10041769 A1 3/2002
DE 10259522 A1 7/2004
(Continued)

OTHER PUBLICATIONS

Iannuzzelli et al. Approaches to MRI Gating Using Multiple Sensors. John Hopkins Apl Technical Digest, vol. 20, No. 2 (1999).*
(Continued)

*Primary Examiner* — Katherine Fernandez
*Assistant Examiner* — Helene Bor

(57) ABSTRACT

The invention relates to a medical unit comprises a 3D radar array for the detection of positional or movement data of objects in an examination space and a processing unit for the evaluation of the detected data, with the processing unit being connected to the medical unit and to the 3D radar array, and with the evaluated data being used to control the medical unit or for post-processing data acquired by the medical diagnostic or therapeutic unit. The invention also relates to a method for improving examination or treatment workflows with the medical unit, comprising: detecting positional or movement data of objects in the examination space by the 3D radar array; generating control commands for the medical unit based on the detected data; and post-processing image or spectroscopy data received by the medical based on the detected data. The medical unit is a medical diagnostic or therapeutic unit.

17 Claims, 2 Drawing Sheets

(51) Int. Cl.
  *A61B 5/00* (2006.01)
  *A61B 6/00* (2006.01)
  *G01S 13/88* (2006.01)
  *A61B 6/03* (2006.01)
  *A61B 17/00* (2006.01)
  *G01S 13/89* (2006.01)

(52) U.S. Cl.
  CPC ........... *A61B 2017/00694* (2013.01); *A61B 2090/061* (2016.02); *G01S 13/89* (2013.01)

(56) References Cited

U.S. PATENT DOCUMENTS

| | | | |
|---|---|---|---|
| 7,389,136 B2* | 6/2008 | Avinash et al. | 600/413 |
| 2007/0014391 A1 | 1/2007 | Hannibal | |
| 2007/0086570 A1 | 4/2007 | Spahn | |
| 2008/0125647 A1 | 5/2008 | Rosengren et al. | |
| 2009/0076379 A1* | 3/2009 | Hamill et al. | 600/424 |
| 2011/0190629 A1* | 8/2011 | Guenther et al. | 600/437 |

FOREIGN PATENT DOCUMENTS

| | | |
|---|---|---|
| DE | 102005049106 A1 | 4/2007 |
| WO | WO 2006091145 A1 | 8/2006 |

OTHER PUBLICATIONS

Paulson et al. Ultra-wideband Radar Methods and Techniques of Medical Sensing and Imaging, SPIE International Symposium on Optics East Boston, MA (2005).*

A Growing number of Applications Boosts mm-Wave Technology; in: High Frequency Electronics (Technology Report); Summit Technical Media; vol. 5, May 2006, p. 52-53.; Magazine; 2006.

* cited by examiner

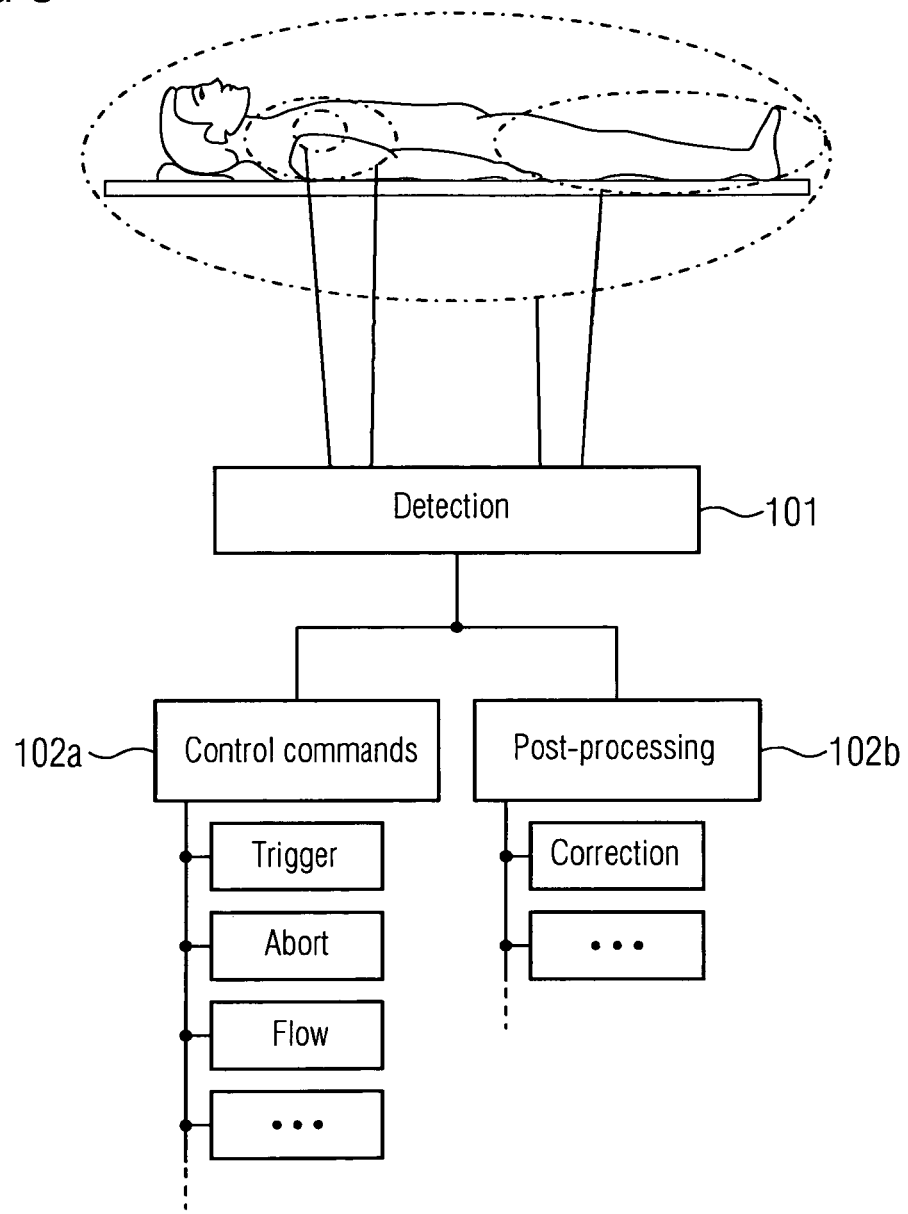

MEDICAL UNIT AND METHOD FOR IMPROVING EXAMINATION AND TREATMENT WORKFLOWS

CROSS REFERENCE TO RELATED APPLICATIONS

This application claims priority of German application No. 10 2008 006 711.3 filed Jan. 30, 2008, which is incorporated by reference herein in its entirety.

FIELD OF THE INVENTION

The invention relates to a medical diagnostic or therapeutic unit. The invention further relates to a method for improving examination and/or treatment workflows with a medical diagnostic or therapeutic unit.

BACKGROUND OF THE INVENTION

For many medical examinations and/or treatments it is advantageous or even necessary to detect and evaluate physiological parameters such as heartbeat or breathing and/or possible movements of a patient.

Examples cited here include captured images of the inside of the body of a patient by means of various modalities such as e.g. computed tomography or magnetic resonance tomography or also therapeutic treatments e.g. with a radiation therapy device The detected data about the physiological parameters of the patient and/or other movements of the patient during the capture of images are used here for example to adjust the acquired image data for movement or indeed to trigger the capturing of images. Frequently the data about movements and/or physiological parameters also provide important information as to a patient's health or state of mind, which can be a determining factor when planning the next course of action even during an examination or treatment.

In order to determine physiological data about a patient, the use e.g. of an ECG to determine the heartbeat, and of a breathing belt to determine breathing, is known. However the necessary application of electrodes and/or of the breathing belt always takes up a certain amount of time, which extends the examination. Moreover these steps are frequently felt by patients to be uncomfortable.

Another parameter that is to be monitored in order to optimize many medical examinations and/or treatments is the movement of the patient's body.

One known manner of monitoring movements of the patient is to arrange so-called light spots at relevant points on the patient, for example at joints and/or principal axis points, and to record the movements of these light spots e.g. with the aid of a video camera. The actual movement is suggested by the data captured in this way for example by means of movement models. This is not always sufficiently precise, since the actual movement of the body is not recorded, but instead movement data from several important measuring points is interpolated.

Moreover, in certain cases it is additionally expedient to monitor the environment of the patient, for example in order to avoid collisions with moving parts of a medical device. For this purpose the use e.g. of cameras in conjunction with object recognition software is known. However it is not always possible to position a camera such that the best-possible perspective on the patient and his/her environment can be achieved.

The radar technique is a known technique for contactless detection of the position and/or movements of objects by emitting electromagnetic signals and receiving signals reflected by the objects. In addition, passive methods are also known in which not reflected radiation, but instead a natural radiation emitted by all objects with a temperature higher than 0 Kelvin, is detected. Using this method temporal resolutions of less than one millisecond and spatial resolutions of up to one millimeter and more can be achieved (see e.g. "A Growing Number of Applications Boosts mm-Wave Technology", High Frequency Electronics, Vol. 5(5), May 2006, p. 52 et seq.). A 3D radar sensor, with which a three-dimensional presentation of the detected objects is possible with a measurement, is known for example from DE 100 41 769.

A method for sensing information about the position and/or movements of a living organism or of part of the inside of a body, particularly for use in a motor vehicle, is known from DE 102 59 522 A1. An objective of the method described in the aforementioned publication is to monitor the breathing and heartbeat of a passenger during a journey.

SUMMARY OF THE INVENTION

One object of the present invention is to specify an apparatus and a method with which examinations and/or treatments can be performed as comfortably and safely as possible for the patient.

Another object of the present invention is to specify an apparatus and a method with which examination and/or treatment workflows of a diagnostic or therapeutic unit can be designed to be as efficient as possible for the operator.

These objects are achieved in accordance with the invention by a medical diagnostic or therapeutic unit and a method as claimed in the claims.

Here a medical diagnostic or therapeutic unit according to the invention comprises at least one 3D radar array for the detection of positional and/or movement data of objects in an examination space of the diagnostic or therapeutic unit and a processing unit for the evaluation of the detected data, with the processing unit being connected to the medical diagnostic or therapeutic unit and to the at least one 3D radar array, and with data evaluated by the processing unit being used to control the medical diagnostic or therapeutic unit and/or for post-processing of data acquired by the medical diagnostic or therapeutic unit.

An inventive method for improving examination and/or treatment workflows with a medical diagnostic or therapeutic unit comprises the following steps:

Detecting positional and/or movement data of objects in an examination space of the medical diagnostic or therapeutic unit by means of at least one 3D radar array, Generating control commands for the medical diagnostic or therapeutic unit on the basis of the detected data and/or Post-processing image or spectroscopy data received by means of the medical diagnostic or therapeutic unit on the basis of the detected data.

Depending on the signal frequencies used, several advantageous steps can be performed with the aid of just one 3D radar array to monitor processes during an examination or treatment of a patient with a medical diagnostic or therapeutic unit. The need for further sensors, such as different cameras, is thereby obviated, and savings are achieved with regard to costs and space. Furthermore just one interface positioned directly between the 3D radar array and the control or evaluation unit of the medical diagnostic or therapeutic unit is sufficient for the coordination e.g. of the control or of an image processing unit of the medical diagnostic or therapeutic unit with the different monitoring data.

It is advantageously possible with the inventive medical diagnostic or therapeutic unit to perform monitoring of heart movements (heartbeat) and/or breathing without the patient having to come into direct contact with the sensors. In this way time-consuming processes that are frequently uncomfortable for the patient, such as the application of ECG electrodes or breathing belts, are no longer necessary. The detected data can be used, e.g. in post-processing of data received by means of the medical diagnostic or therapeutic unit, in order to correct movement artifacts in image data for example. Furthermore information can be obtained from the data detected by means of a 3D radar array, on the basis of which control signals can be generated to control the medical diagnostic or therapeutic unit, for example to trigger the capturing of images. Conclusions as to the position of the patient can additionally be drawn from the data detected in this way, and on the basis of this data a treatment or examination can, if necessary, be halted or interrupted.

Furthermore a 3D radar array also allows for monitoring of movements of body parts or of the entire body of a patient or of another object. In this way it is possible on the one hand e.g. to increase a patient's safety by evaluating the detected data such that collisions between the patient and other objects can be avoided. Of course, collisions between different objects, e.g. between local coils or retaining and/or supporting apparatuses on a patient couch and the trim panel components of the medical diagnostic or therapeutic unit, can also be prevented. In the case of an upcoming collision in particular, a control command can be generated that aborts the examination or treatment or halts the dangerous movement.

On the other hand, it is possible by means of just one 3D radar array to determine the position and dimensions of different objects as well as of the patient's body, which enables an estimate of body mass to be performed, which can be used for a precise calculation of SAR limits ("Specific Absorption Rate") and supports the position resolution of examinations or treatments with the medical diagnostic or therapeutic unit.

Thus the comprehensive monitoring of a patient is possible with the aid of 3D radar arrays.

Suitable medical diagnostic or therapeutic units include in particular medical imaging units, such as computed tomography (CT) scanners or magnetic resonance tomography or spectroscopy (MRT, MRS) devices, or radiation therapy devices.

A 3D radar array of the medical diagnostic or therapeutic unit can advantageously be adjusted to different frequency ranges. In other words it is possible to vary the working frequency of the signals emitted by the 3D radar array. In this way different types of movements can easily be detected by the 3D radar array at different distances and with different depths of penetration into the object. Furthermore non-relevant objects can also be penetrated by the radiation so that putatively concealed objects that are of interest can also be detected.

In a further advantageous embodiment a 3D radar array of the medical diagnostic or therapeutic unit can simultaneously operate in different frequency ranges e.g. in the manner of a so-called "stealth radar". Although this requires a greater outlay in terms of signal processing, simultaneous monitoring of different movement types at different distances by the 3D radar array is also possible.

In an especially advantageous embodiment the medical diagnostic or therapeutic unit comprises several 3D radar arrays, each of which operates with different frequencies. In this case a 3D radar array that is suited to the currently-desired monitoring is put into operation. Thus a comprehensive monitoring of movements and positions of objects in the examination space of the medical diagnostic or therapeutic unit is possible by means of simple and therefore particularly cost-effective 3D radar arrays.

The advantages and embodiments that relate to the apparatus apply analogously to the method.

BRIEF DESCRIPTION OF THE DRAWINGS

Further advantages and details of the present invention will emerge from the exemplary embodiments described below and with the aid of the drawings.

Examples are provided below, which do not constitute any limitation of the invention, and in which

FIG. 3 shows a schematic diagram to clarify a method according to the invention.

DETAILED DESCRIPTION OF THE INVENTION

Figure 1:
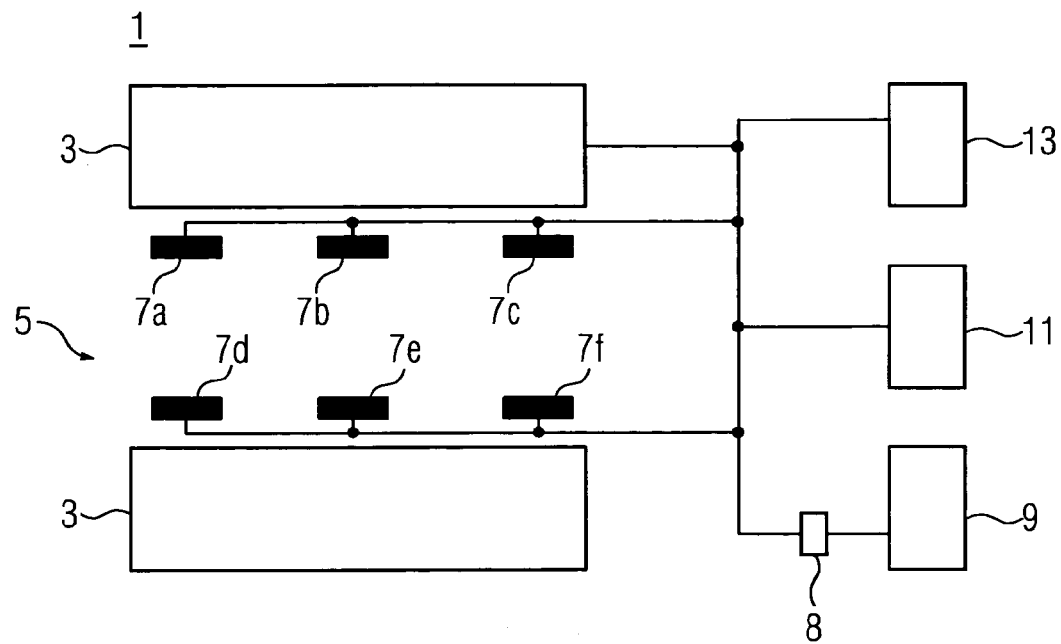
FIG. 1 shows a schematic drawing of a first embodiment of a medical diagnostic or therapeutic unit according to the invention.

FIG. 1 schematically shows a first embodiment of a medical diagnostic or therapeutic unit 1 according to the invention. Merely as an example, the medical diagnostic or therapeutic unit is shown here by one magnet unit 3 of a known magnetic resonance device. The magnet unit 3 at least partially surrounds an examination space 5 of the medical diagnostic or therapeutic unit.

However the medical diagnostic or therapeutic unit can also be another known medical imaging unit, such as a CT device, or a known radiation therapy device.

The magnetic resonance unit 3 of the magnetic resonance device forms a kind of cavity around the examination space 5. In the example shown, six 3D radar arrays 7a-7f are arranged in the cavity that surrounds the examination space 5. For example, the 3D radar arrays 7a-7f can be arranged on an interior trim panel of the examination space 5. The 3D radar arrays can be located both on the trim panel, such that they are accessible from the outside, and they can also be covered by the trim panel.

With just one 3D radar array a spatial i.e. three-dimensional image of detected contours and/or movements can be formed. The corresponding measurement method can accordingly be based on both time measurement and a phase/frequency measurement. Both continuous wave (CW) radar and impulse radar can be used. The use of a passive radar, which detects a natural radiation in the millimeter wavelength range that is emitted or reflected by all objects, is also conceivable.

The 3D radar array is advantageously realized so as to be able to detect accelerations in the movements in the examination space of the medical diagnostic or therapeutic unit. This can be achieved in particular by using the Doppler effect. Knowledge of the acceleration and velocity of a detected object, in particular in procedures for the post-processing of image data captured by means of the medical diagnostic or therapeutic unit, enables a particularly good reduction and correction of image artifacts that have arisen as a result of movements during the capture of image data.

The 3D radar arrays 7a-7f are arranged so that, depending on the desired type of monitoring, an area of a corresponding 3D radar array 7a-7f to be monitored is covered. For example, the central measurement zone of the medical diagnostic or therapeutic unit can be monitored particularly well by at least one 3D radar array 7b, 7e arranged centrally in the examination space 5 e.g. for monitoring the positions of objects or devices being examined or specific body parts or organs of a patient. However, an entry and/or exit of the examination space of the medical diagnostic or therapeutic unit can be monitored more easily by means of at least one 3D radar array 7a, 7c, 7d, 7f arranged close to the entry and/or exit e.g. to avoid collisions. The precise arrangement also depends e.g. on the corresponding detection area and on the direction of a 3D radar array that is being used.

Each 3D radar array 7a-7f is connected to a processing unit 9 in which the data detected by the 3D radar arrays 7a-7f can be evaluated and/or processed further. Furthermore the processing unit 9 is connected to a control unit 11 and/or an image processing unit 13 of the medical diagnostic or therapeutic unit. If at least one 3D radar array is adjustable to different frequencies, said 3D radar array is also connected to a frequency-regulating unit 8 with the aid of which a desired frequency can be selected. The processing unit 9, the frequency-regulating unit, the control unit 11 and the image processing unit 13 can also be realized as a single unit or at least partially integrated into one another.

More details on the evaluation and further processing of the data detected by 3D radar arrays will be provided below.

Figure 2:
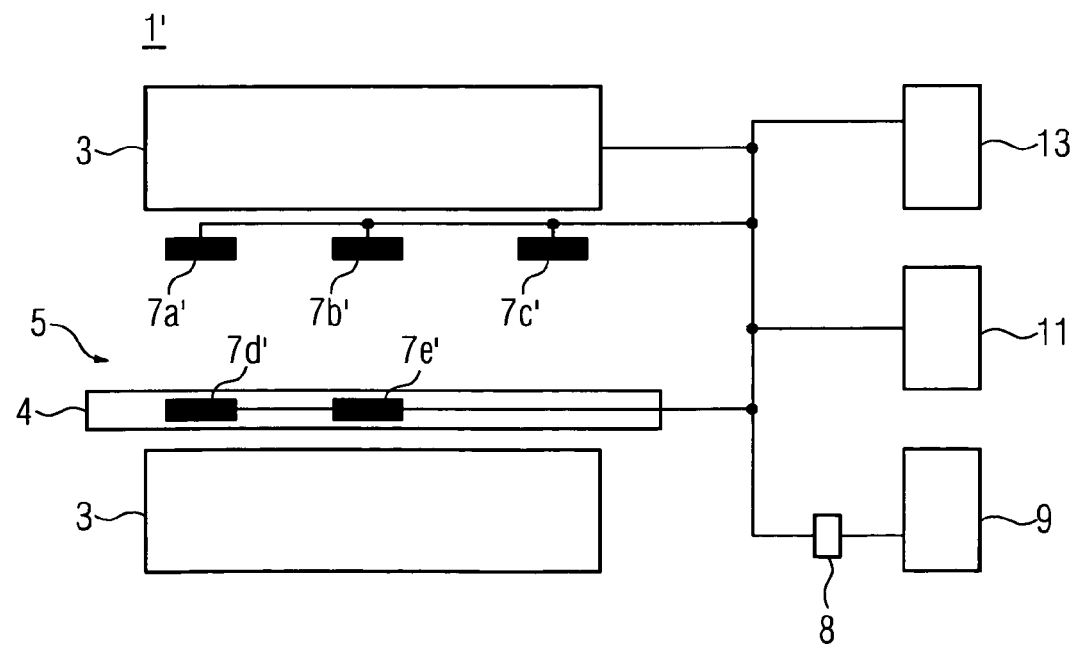
FIG. 2 shows a schematic drawing of a second embodiment of a medical diagnostic or therapeutic unit according to the invention.

FIG. 2 schematically shows a further embodiment of the present invention. Once again the medical diagnostic or therapeutic unit 1 is sketched out with just one magnet unit 3. FIG. 2 additionally shows an examination couch/patient couch 4 on which the patient to be examined or treated can be positioned and introduced into the examination space 5 of the medical diagnostic or therapeutic unit 1'.

As was the case for the embodiment shown in FIG. 1, in the embodiment shown in FIG. 2 3D radar arrays 7a'-7c' are arranged in the environment of the examination space 5 such that desired monitoring steps can be performed. This exemplary embodiment includes 3D radar arrays 7d'-7e' being arranged in the examination couch 4. These 3D radar arrays are particularly suited, because of their arrangement close to the upper part of a patient's body for example, to the monitoring of heart movements (heartbeat) and/or breathing movements. A further advantage of the arrangement of 3D radar arrays 7d'-7e' in an examination couch 4 is that monitoring by means of this 3D radar array can also easily be performed while the examination couch 4 is being moved, and in particular without changing the direction of the 3D radar arrays 7d'-7e'. Even before the start of an examination or treatment with the medical diagnostic or therapeutic unit, if the examination couch 4 remains located outside the examination space 5 within the medical diagnostic or therapeutic unit, monitoring can be performed by means of the 3D radar arrays 7d'-7e'.

As in the first exemplary embodiments the 3D radar arrays 7a'-7e' are connected to a processing unit 9 and possibly to a frequency-regulating unit and indirectly or directly to a control unit 11 and an image processing unit 13 of the medical diagnostic or therapeutic unit 1'.

The 3D radar arrays 7a-7f, 7a'-7e' are in any case realized such that they do not assume any spurious interactions with the respective medical diagnostic or therapeutic unit. In the case of a magnetic resonance device as a medical diagnostic or therapeutic unit, this means in particular that the 3D radar arrays 7a-7f, 7a'-7e' and any associated data lines and/or supply lines are produced using non-magnetic materials, in particular those that do not contain ferrites, and/or are shielded accordingly. It is furthermore advantageous that a 3D radar array can be equipped in this case with a filter that prevents the high-frequency radiation of the magnetic resonance device from penetrating the 3D radar array, but that allows the radiation emitted by the 3D radar array to filter through.

In the case of a medical diagnostic or therapeutic unit that emits radiation for the purpose of examination or therapy, such as e.g. CT devices or radiation therapy devices, the 3D radar arrays 7a-7f, 7a'-7e' are protected in particular against the harmful influences of the radiation used. In the simplest case this can be achieved by their being arranged outside of the radiation.

Another simple protective measure against spurious interactions would be to switch between operating the medical diagnostic or therapeutic unit for the examination and/or treatment of a patient and operating the 3D radar array(s) for the monitoring of positional and/or movement data, in the examination space of the medical diagnostic or therapeutic unit.

A schematic diagram to clarify a method according to the invention is sketched out in FIG. 3. The diagram shows the steps for detecting positional and/or movement data 101 for monitoring a patient, whereby the positional and/or movement data can comprise e.g. heart movements, breathing movements, movements of the body and/or object, as well as their positions, as has been sketched out at the top of FIG. 3.

Control commands that control the medical diagnostic or therapeutic unit can be generated on the basis of the detected data (Step 102a) and/or data received by means of the medical diagnostic or therapeutic unit, in particular image or spectroscopy data, can be post-processed on the basis of the detected data (Step 102b).

In particular the control commands can comprise triggering the medical diagnostic or therapeutic unit, or they can abort or pause an examination and/or treatment with the medical diagnostic or therapeutic unit, or the flow of an examination or treatment can be influenced by the control commands generated. Post-processing of data received by means of the medical diagnostic or therapeutic unit can comprise in particular a correction of movement artifacts. On the basis of the data detected by means of the 3D radar arrays, a treatment or examination with the medical diagnostic or therapeutic unit, and the results of said treatment or examination, can thus be influenced in a positive manner.

Several more exemplary applications are listed below.

An advantageous exemplary application for a medical diagnostic or therapeutic unit 1, 1' with at least one 3D radar array 7a-7f, 7a'-7e' for the detection of positional and/or movement data of objects in an examination space of the medical diagnostic or therapeutic unit, and with a processing unit 9 for the evaluation and further processing of the detected data, is the detection of movements, in particular pumping movements of a heart of a patient e.g. to trigger cardiac examinations and/or to correct movement artifacts in the capture of images of the heart. In this case for example the pumping movements of the heart are recorded by directing the monitoring 3D radar array appropriately and using radar radiation at suitable frequencies, and said pumping movements are evaluated by means of the processing unit 9. On the basis of this data for example control commands for the temporal coordination of a measurement or treatment of the heart can be generated in the control unit 11 using the heartbeat, with said control commands controlling the medical diagnostic or therapeutic unit accordingly. Alternatively information from the evaluated data can be supplied to an image processing unit 13 on the basis of which a correction of movement artifacts in image data of the heart captured by means of the medical diagnostic or therapeutic unit can be performed in accordance with customary rules.

Breathing movements of a patient can also be detected and used analogously by directing and using appropriate radar frequencies in a corresponding manner.

A further exemplary application is the monitoring of the physiological condition of a patient. Once again the heartbeat, breathing movements and/or e.g. blinking frequency of the patient can accordingly be monitored by means of one or several 3D radar arrays. In this case the data evaluated with the processing unit 9 can be used on the one hand, for example if there are signs of growing anxiety in the patient, to send a control command from the control unit 11 to the medical diagnostic or therapeutic unit to abort the examination or treatment. On the other hand this data can also be of use in a subsequent diagnosis after the examination or treatment.

A further possible form of monitoring is the detection of movements of body parts or of the entire body of a patient e.g. during an examination or treatment by directing the monitoring 3D radar array appropriately and using appropriate radar frequencies. The data on completed translations and/or rotations of e.g. the extremities or the head thus acquired can again be evaluated in the processing unit 9. On the basis of this data once again e.g. control commands can be generated in the control unit 11 for example in order to control movable parts of the medical diagnostic or therapeutic unit, such as e.g. a patient couch 4 or a rotatable therapeutic radiation source in the event of the medical diagnostic or therapeutic unit being realized as a radiation therapy device, in order to avoid collisions, and/or in a similar manner to the information described above, in order to post-process image data in the image processing unit 13.

In a similar manner it is also possible by means of the at least one 3D radar array to determine the dimensions/size, proportions and/or position of a patient relative to the medical diagnostic or therapeutic unit. On the basis of this data it is possible, for example by means of the processing unit 9, to perform estimates of weight and/or SAR (Specific Absorption Rate), with the aid of which for example an irradiation or measurement duration of a treatment or examination with the medical diagnostic or therapeutic unit can be controlled. Furthermore the position data can be used to improve a position resolution of an examination or treatment since said data comprises the precise position of an examined or treated region of the body relative to the medical diagnostic or therapeutic unit.

In particular in the case of a magnetic resonance device as the medical diagnostic or therapeutic unit it is furthermore advantageous to detect, by means of one or several 3D radar arrays in the manner already described, a position of local coils relative to a patient. Such data can be evaluated by the processing unit 9 such that, by means of a known sensitivity and/or effect profile of the corresponding local coil, SAR monitoring can be improved further. With the knowledge thus gained it is furthermore possible to shorten acquisition times e.g. when using a known parallel imaging technique (e.g. iPAT, or "integrated parallel acquisition technique"). In parallel imaging techniques fewer phase encoding steps are performed than is conventionally the case, which in practice entails a reduction in the information measured. However this is offset against knowledge about the local coils used, e.g. their sensitivity profiles. Thus with a more-precise knowledge of the position of a local coil relative to the patient, the acceleration of a measurement by means of a parallel acquisition technique e.g. by a suitable selection of receiving coil elements can be improved, and thus the acquisition time can be shortened.

By using different frequencies the depth and/or strength of penetration of the radiation of a 3D radar array can be varied. It is thus possible e.g. to penetrate local coils or the clothing of a patient and to obtain in a contactless manner a realistic three-dimensional model of positional and/or movement data through objects or body parts that are in the conventional sense invisible from the outside. So it is possible not only to monitor parts or the whole of a patient's body or other objects, such as patient couches or local coils; internal organs such as e.g. a patient's heart can also be monitored. This effect can be extended further if special materials, which especially reflect the radiation of a 3D radar array and/or allow it to pass through, are used for the patient's clothing or for the trim panel of an examination space of the medical diagnostic or therapeutic unit or of other parts of the medical diagnostic or therapeutic unit, for example.

Thus through the appropriate selection of the radar frequencies used certain objects can be rendered "visible" or "invisible" as required.

The invention claimed is:

1. A medical unit, comprising:
    a medical device;
    a 3D radar array that detects positional data of an object in an examination space of the medical device;
    a processing unit that monitors a movement of the object based on the detected data;
    a control unit that controls the medical device based on the monitored movement of the object; and
    a post-processing unit that post-processes medical data acquired by the medical device, wherein the post-processing comprises of correcting movement artifacts based on the monitored movement of the object.

2. The medical unit as claimed in claim 1, wherein the 3D radar array is arranged in a patient couch of the medical device.

3. The medical unit as claimed in claim 1, wherein the 3D radar array is arranged in a cavity that surrounds the examination space of the medical device.

4. The medical unit as claimed in claim 1, wherein the 3D radar array adjustably operates in different frequency ranges.

5. The medical unit as claimed in claim 4, wherein the 3D radar array simultaneously operates in the different frequency ranges.

6. The medical unit as claimed in claim 5, further comprising a plurality of 3D radar arrays that are operated in the different frequency ranges.

7. The medical unit as claimed in claim 1, wherein the 3D radar array does not undergo any spurious interactions with the medical device.

8. The medical unit as claimed in claim 1, wherein the processing unit, the control unit, and the post-processing unit are integrated into a single unit.

9. The medical unit as claimed in claim 1, wherein the medical device is a medical imaging device.

10. The medical unit as claimed in claim 1, wherein the medical device is a medical diagnostic or therapeutic device.

11. A method for improving workflows of a medical unit comprising a medical device, comprising:
    detecting movement data of an object in an examination space of the medical device by a 3D radar array;

monitoring a movement of the object based on the detected data;

generating a control command for the medical device based on the monitored movement of the object; and post-processing medical data received the medical device, wherein the post-processing comprises correcting movement artifacts of the medical data based on the monitored movement of the object.

12. The method as claimed in claim 11, wherein the control command triggers the medical device.

13. The method as claimed in claim 11, wherein the control command pauses or aborts an examination or treatment with the medical device.

14. The method as claimed in claim 11, wherein the control command controls a temporal flow of an examination or treatment with the medical device.

15. The method as claimed in claim 11, wherein the movement data comprises data selected form the group of: a heart movement of a patient, a breathing movement of the patient, movement of the patient, a dimension of a body part of the patient, and a position of the body part of the patient.

16. The method as claimed in claim 11, wherein the workflow is an examination or treatment workflow of the medical device.

17. The method as claimed in claim 11, wherein the medical data comprises image data or spectroscopy data.

* * * * *